(12) United States Patent
Oka et al.

(10) Patent No.: US 7,326,384 B2
(45) Date of Patent: *Feb. 5, 2008

(54) METHOD AND APPARATUS FOR DETECTING PHYSICOCHEMICAL CHANGES EMITTED BY BIOLOGICAL SAMPLE

(75) Inventors: Hiroaki Oka, Hirakata (JP); Nobuhiko Ozaki, Ikoma (JP); Hirokazu Sugihara, Katano (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 890 days.

This patent is subject to a terminal disclaimer.

(21) Appl. No.: 10/208,547

(22) Filed: Jul. 29, 2002

(65) Prior Publication Data

US 2003/0022387 A1    Jan. 30, 2003

(30) Foreign Application Priority Data

Jul. 30, 2001    (JP)    ............................. 2001-230624

(51) Int. Cl.
   *B32B 5/02*    (2006.01)
(52) U.S. Cl. .............................. 422/82.01; 422/82.02; 204/403.01; 204/403.06; 204/415; 436/149; 436/150
(58) Field of Classification Search ............... 422/68.1, 422/82.01, 82.02; 435/287.1; 204/403.07, 204/400, 403.01, 403.06, 415; 436/149, 436/150
See application file for complete search history.

(56) References Cited

U.S. PATENT DOCUMENTS

| | | | | |
|---|---|---|---|---|
| 4,556,623 A | | 12/1985 | Tamura et al. | |
| 4,789,436 A | * | 12/1988 | Greenbaum | ................. 205/778 |
| 5,000,180 A | * | 3/1991 | Kuypers et al. | ............. 600/360 |
| 5,563,067 A | | 10/1996 | Sugihara et al. | |
| 6,068,818 A | * | 5/2000 | Ackley et al. | ................. 422/50 |
| 6,099,803 A | * | 8/2000 | Ackley et al. | ............. 422/68.1 |
| 6,225,059 B1 | * | 5/2001 | Ackley et al. | ................. 435/6 |
| 6,254,827 B1 | * | 7/2001 | Ackley et al. | ............. 422/68.1 |
| 6,488,829 B1 | * | 12/2002 | Schroeder et al. | ..... 204/403.01 |
| 6,540,961 B1 | * | 4/2003 | Ackley et al. | ................. 422/50 |
| 6,682,649 B1 | * | 1/2004 | Hansen et al. | ........... 205/777.5 |
| 6,726,880 B1 | * | 4/2004 | Ackley et al. | ............. 422/68.1 |
| 6,756,223 B2 | * | 6/2004 | Roberts et al. | ........... 435/287.2 |
| 6,821,729 B2 | * | 11/2004 | Ackley et al. | ................. 435/6 |

FOREIGN PATENT DOCUMENTS

| | | |
|---|---|---|
| EP | 0 247 850 A | 12/1987 |
| EP | 0247850 A1 | 12/1987 |
| JP | 58-171659 A | 10/1983 |
| WO | WO 91-02975 A | 3/1991 |
| WO | WO 99-66329 A | 12/1999 |
| WO | WO 99/66329 A1 | 12/1999 |
| WO | WO 01-25769 A | 4/2001 |

OTHER PUBLICATIONS

Corresponding Korean Office Action dated Apr. 29, 2005.
European Search Report dated Nov. 27, 2003.

* cited by examiner

*Primary Examiner*—Jill Warden
*Assistant Examiner*—Dwayne K Handy
(74) *Attorney, Agent, or Firm*—Snell & Wilmer L.L.P.

(57) ABSTRACT

A device for detecting a physicochemical change in a biological sample comprising at least one measuring electrode provided by causing a conductive material to enter into a porous film, and a conductor connected to the measuring electrode.

24 Claims, 15 Drawing Sheets

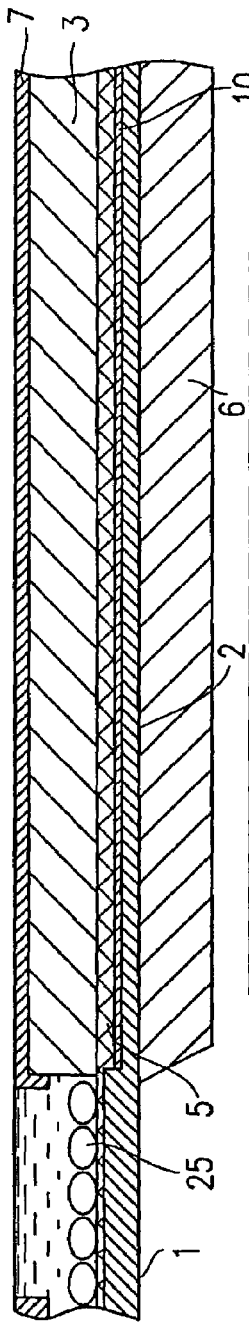
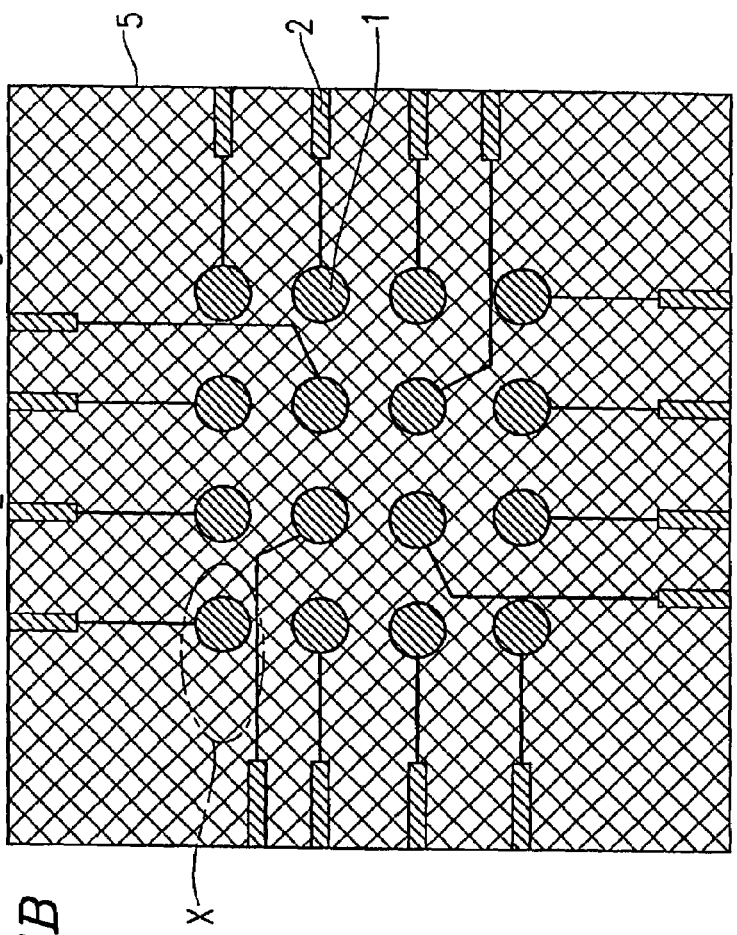
FIG. 7A
FIG. 7B

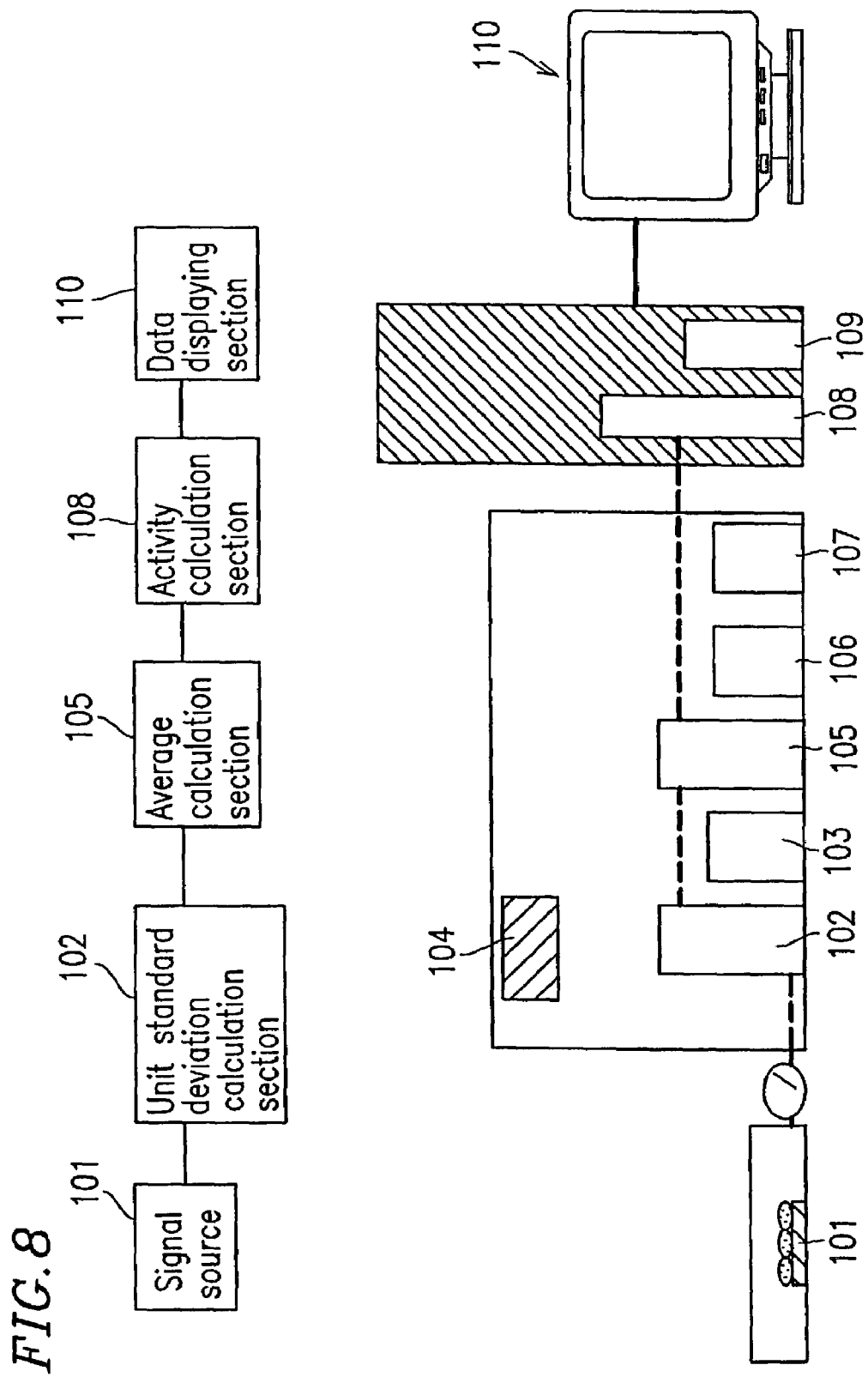

METHOD AND APPARATUS FOR DETECTING PHYSICOCHEMICAL CHANGES EMITTED BY BIOLOGICAL SAMPLE

BACKGROUND OF THE INVENTION

1. Field of the Invention

The present invention relates to a device and method for measuring physicochemical changes in a biological sample, typically a cell, and an apparatus comprising the device. More particularly, the present invention relates to a device and method for measuring physicochemical changes in a cell correlating with a macroscopic level of ion channel activity of the whole cell, and an apparatus comprising the device. The present invention also relates to a method and device for screening drugs.

2. Description of the Related Art

Conventionally, physical signals or chemical signals emitted in association with the activity of a biological sample, such as a cell, are measured by a measurement apparatus for capturing changes in an electrical signal, the fluorescence intensity of a fluorescence indicator taken up by a biological sample, or the like, as a digital signal.

For example, when the ion channel activity of a cell is measured, a level of a single ion channel is measured by an electrophysiological measurement apparatus using a microelectrode probe (e.g., patch clamp) and a specialized control apparatus as follows. The apparatus captures the amount of electricity passing through an ion channel of a cell as a digital signal and, based on amount of electricity, calculates the duration, timing, number of times, and the like of opening or closing of the ion channel. In this technique, a microelectrode probe is inserted into a cell and electric current passing through a biological sample is measured. The technique is therefore called an intracellular recording method.

In a patch clamp technique, a small portion (patch) of cell membrane is attached to a tip portion of a micropipette with a microelectrode probe, and is used to electrically record ion transportation through a single ion channel protein. The patch clamp technique is one of a few number of cell biological techniques which can be used to investigate the function of a single protein in real time (see, e.g., Molecular Biology of the Cell, 3rd Ed., Garland Publishing, Inc., New York, 1994, Japanese Version, translation supervised by Keiko Nakamura et al., pp. 181-182, 1995, Kyoikusha).

The ion channel activity of a whole cell can also be measured by a fluorescence measurement method capturing the amount of ions flowing into the cell as a digital signal.

In a fluorescence measurement technique, a light emitting indicator or a fluorescent pigment which emit light in accordance with the concentration of a specific ion, is combined with an up-to-date image processing method (e.g., a fluorescence image of a cell is captured by a CCD camera or the like, and the movement of ions in the cell is monitored) to measure the electrical activity of the entire cell.

The patch clamp technique requires special techniques for preparation, manipulation and the like of a micropipette, and much time for measuring one sample. Therefore, the patch clamp technique is not suitable for screening a large quantity of candidate compounds for a drug at high speed. The fluorescence measurement technique can screen a large quantity of candidate compounds for a drug at high speed. However, the fluorescence measurement technique requires a step of staining a cell. During measurement, pigments cause high background noise, and the fluorescence intensity decreases with time, resulting in poor signal to noise ratio (S/N).

Another technique for observing an electrochemical change in a biological sample, is disclosed in JP No. 2949845, U.S. Pat. Nos. 5,810,725, 5,563,067, Japanese Laid-Open Publication No. 9-827318, WO 01/25769 A2, U.S. Pat. No. 5,187,069, WO 98/54294, WO 99/66329, WO 99/31503, and the like, in which a substrate provided with multiple electrodes is employed.

JP No. 2949845, U.S. Pat. Nos. 5,810,725, 5,563,067, and Japanese Laid-Open Publication No. 9-827318 disclose an integrated multiple electrode comprising microelectrodes prepared by photolithography on a glass substrate and capable of measuring electrical changes in cells, and a measurement system using the same.

WO 01/25769 A2 discloses a substrate in which an insulating substrate provided with through holes and a biological sample, such as a cell containing an ion channel, is placed on the through holes so that a gigaseal is provided on the surface of the insulating substrate including the cell; a reference electrode and a measuring electrode, which are provided in two respective domains separated by the gigaseal, can be used to measure electric current generated by ions passing through an ion channel of the cell.

U.S. Pat. No. 5,187,069 discloses a device capable of monitoring the growth of cells by culturing the cells on electrodes and measuring impedance changes.

WO 98/54294 discloses a device in which cells are adhered onto a planar electrode and an electrical signal thereof is measured.

WO 99/66329 discloses a device for observing the activity of cells on a porous material by measuring resistance or impedance changes, and an assay using the same.

WO 99/31503 discloses a method in which a substrate provided with through holes is employed, patch clamps are established by trapping cells with the through holes, and changes in electric current are measured.

Any of the above-described conventional techniques are characterized in that the electrical activity of cells is determined on a planar electrode, and small through holes are provided in an insulating substrate so that patch clamp is formed with cells and, the substrate, whereby electric current generated by ions passing through an ion channel can be monitored. However, when a planar electrode is employed, a signal emitted from a biological sample leaks into solution so that the sensitivity of the measurement is disadvantageously reduced. In the method in which small through holes are provided in an insulating substrate so that patch clamps are formed with cells and the holes, the possibility of forming gigaseal patch clamps is low. Moreover, the cell membrane must be destroyed or physically injured to form patch clamp, so that it is not possible to measure the activity of intact cells. Patch clamp formation techniques also have a difficulty in adjusting suctioning pressure for a biological sample. Multiple channels would impractically require multiple pressure adjusting mechanisms. In these regards, conventional planar electrodes are suitable for high-speed drug screening but have poor sensitivity. The insulating substrate having small through holes is not suitable for high-speed drug screening. For similar reasons, an automated patch clamping robot requires much time for sample processing and is not suitable for high-speed drug screening.

SUMMARY OF THE INVENTION

The present invention is provided to solve the above-described conventional problems. The object of the present invention is to provide a method for easily and reliably detecting a minute change in a physiochemical signal emitted by a biological sample, which cannot be detected by conventional extracellular recording methods, and an apparatus using the same for measuring an electrochemical change in a biological sample. Particularly, the object of the present invention is to provide a method for measuring an ion channel activity of a whole cell, i.e., a physicochemical change emitted by a cell, in which a simple device, which does not require a specialized control apparatus, is employed and cells are simply placed on a porous film in a chamber, so that the cells can be easily measured in a short time without a gigaseal being provided between the cells and an insulating substrate (support substrate), and in which since no chemical substance is employed, it is not necessary to consider any side effect or any change in fluorescence sensitivity over time; and high-speed drug screening using the method.

The present invention relates to a device for detecting a physiochemical change in a biological sample. The device comprises at least one measuring electrode provided by causing a conductive material to enter into a porous film, and a conductor connected to the measuring electrode.

Preferably, the device further comprises a support substrate for supporting the porous film, a cell isolation portion provided on a surface of the porous film, for defining at least one chamber for accommodating a biological sample, and a suction portion to be coupled in fluid communication with the biological sample in the chamber through the porous film. The measuring electrode is provided on a rear side of the porous film under the chamber.

Preferably, the measuring electrode is provided by sputtering a conductive material onto the porous film, and the conductor is provided by sputtering or printing a conductive material onto a mask layer provided on the porous film.

Preferably, each measuring electrode and the conductor connected thereto are insulated from the other measuring electrodes and the conductors thereto, so that the measuring electrodes can perform detection independently from each other.

Preferably, each measuring electrode and the conductor connected thereto are insulated from the other measuring electrodes and the conductors thereto by an insulating resin injected to the porous film.

Preferably, each measuring electrode and the conductor connected thereto are insulated from the other measuring electrodes and the conductors thereto by destroying a porous structure of surroundings of each measuring electrode and the conductor connected thereto with heat treatment, a laser or pressure.

Preferably, each measuring electrode and the conductor connected thereto are insulated from the other measuring electrodes and the conductors thereto by adhesive for adhering the cell isolation portion provided on the porous film to the porous film.

The present invention also relates to the device further comprising a support substrate for supporting the porous film, a cell isolation portion provided on a surface of the porous film, for defining at least one chamber for accommodating the biological sample, and at least one reference electrode. The measuring electrode is provided on a rear side of the porous film under the chamber, a reference electrode is provided on an inner wall of the chamber, and a conductor connected to the reference electrode is provided on an upper side of the cell isolation portion by patterning.

Preferably, the cell isolation portion is made of an insulating material.

Preferably, the cell isolation portion is made of an insulating material.

Preferably, the porous film is made of an insulating material and 1 to 10000 μm in thickness.

Preferably, the support substrate is 10 to 10000 μm in thickness.

Preferably, the support substrate is adhered to the suction portion, interposing an adhesive layer. The adhesive layer is made of an insulating material and 10 to 10000 μm in thickness.

Preferably, the device of the present invention comprises a plurality of measuring electrodes and a plurality of chambers, and the suction portion simultaneously or separately suctions each chamber.

Preferably, the measuring electrode and the conductor are made of a material selected from the group consisting of metals, conductive plastics, and conductive rubbers.

Preferably, the metal is selected from the group consisting of gold, platinum, copper, silver, silver-silver chloride, and platinum-platinum black.

Preferably, the reference electrode is made of a metal selected from the group consisting of gold, platinum, copper, silver, silver-silver chloride, and platinum-platinum black.

According to one aspect of the present invention, a method for measuring a physicochemical change in a biological sample of interest, comprises the steps of providing at least one reaction system for measuring a physiochemical characteristic of the biological sample of interest, placing the biological sample of interest in the reaction system, and detecting a change in the physiochemical characteristic of the biological sample of interest. The reaction system comprises the above-described device, an arrangement and an environment or a characteristic of the reference electrode and the measuring electrode are adapted to characterize a change in the physiochemical characteristic of the biological sample of interest.

Preferably, the arrangement and the environment or the characteristic are volumes of domains, the reference electrode and the measuring electrode being provided in the respective domains, and the volume of the domain provided with the measuring electrode is smaller than the volume of the domain provided with the reference electrode.

Preferably, the arrangement and environment or characteristic are impedances of the reference electrode and the measuring electrode, and the impedance of the measuring electrode is lower than the impedance of the reference electrode.

Preferably, the arrangement and environment or characteristic are frequency characteristics of the reference electrode and the measuring electrode, the impedance of the measuring electrode at about 10 Hz to about 10 kHz is smaller than the impedance of the reference electrode at about 10 Hz to about 10 kHz.

Preferably, the arrangement and environment or characteristic are the amounts of electrolyte immersing the reference electrode and the measuring electrode, and the amount of the electrolyte immersing the reference electrode is greater than the amount of the electrolyte immersing the measuring electrode.

Preferably, the amount of the electrolyte immersing the reference electrode is about 5 or more times as great as the amount of the electrolyte immersing the measuring electrode.

Preferably, the impedance of the reference electrode is about 5 or more times as great as the impedance of the measuring electrode.

Preferably, the reaction system has an arrangement and an environment or a characteristic selected from the group consisting of the impedance of the reference electrode: the impedance of the measuring electrode=5:1 and the volume of the electrolyte immersing the reference electrode: the volume of the electrolyte immersing the measuring electrode=5:1.

Preferably, the step of detecting the physicochemical characteristic of the biological sample of interest comprises the steps of (a) recording a physiochemical signal emitted from the biological sample of interest as a time-series signal value, (b) sampling the time-series signal value to obtain a plurality of groups of extracted data consisting of a plurality of values, and calculating a standard deviation of each of the plurality of groups, (c) calculating an average of each of the standard deviations, and (d) detecting a change in the physicochemical characteristic of the biological sample based on the average.

Preferably, the step of detecting the physicochemical characteristic of the biological sample of interest comprises the steps of (a) recording a physiochemical signal emitted from the biological sample of interest as a time-series signal value, (b) sampling the time-series signal value to obtain a plurality of groups of extracted data consisting of a plurality of values, and calculating a standard deviation of each of the plurality of groups, (c) dividing the standard deviations into a plurality of classes having a predetermined size of standard deviation as a unit, and obtaining a distribution indicating physicochemical characteristics of the plurality of groups of extracted data belonging to the classes, (d) approximating the distribution to a normal distribution, (e) calculating an average and a half-width of the resultant normal distribution, (f) optionally repeating (b) to (e), and (g) detecting a change in the physicochemical characteristic of the biological sample based on the average and half-width.

Preferably, the steps (b) to (e) are repeated and the number of the time-series signal values to be sampled is changed in each repetition.

Preferably, before the step (b), the method further comprises adding up the time-series signal values emitted by a plurality of biological samples of interest provided in the reaction systems.

Preferably, before the step (a), the method further comprises simultaneously stimulating the plurality of the biological samples of interest.

Preferably, the step of detecting a change in the physicochemical characteristic of the biological sample of interest, comprises (a) recording a physiochemical signal emitted from the biological sample of interest as a time-series signal value, (b) sampling the time-series signal value to obtain a plurality of groups of extracted data consisting of a plurality of values, and calculating a standard deviation of each of the plurality of groups, (c) dividing the standard deviations into a plurality of classes having a predetermined size of standard deviation as a unit, and obtaining a distribution indicating physicochemical characteristics of the plurality of groups of extracted data belonging to the classes, (d) approximating the distribution by curvilinear approximating analysis selected from the group consisting of exponential decreasing analysis, exponential increasing analysis, Gaussian distribution, Lorentz distribution, σ analysis, multiple peak analysis, and nonlinear analysis, and (e) detecting a change in the physicochemical characteristic of the biological sample based on gradients before and after a peak on the approximated curve obtained by the step (d).

Preferably, the sampling in the step (b) is carried out in a time-series manner.

Preferably, the sampling in the step (b) is carried out at random.

Preferably, the sampling in the step (b) is carried out a plurality of times from initial data a in a time-series manner and a plurality of times from data b recorded at a predetermined time after the initial data a in a time-series manner.

Preferably, the sampling in the step (b) is carried out a plurality of times from initial data a in a time-series manner and a plurality of times from data b recorded at a predetermined time after the initial data a in a time-series manner.

Preferably, the step of detecting a change in the physicochemical characteristic of the biological sample of interest, comprises (a) recording a physiochemical signal emitted from the biological sample of interest as a time-series signal value, (b) sampling the time-series signal value to obtain a plurality of groups of extracted data consisting of a plurality of values, and calculating a standard deviation of each of the plurality of groups, (c) sampling the resultant standard deviations to obtain a plurality of groups of extracted standard deviations consisting of a plurality of values, and calculating an average of each of the plurality of groups of extracted standard deviations, and (e) obtaining an index value detecting a change in the physicochemical characteristic of the biological sample based on a time of occurrence of the time-series signal value when the average reaches a predetermined threshold.

Preferably, the biological sample of interest is a cell, and the physiochemical signal is a signal associated with activation of an ion channel or receptor of the cell, or actuation of an intracellular signal transduction system.

Preferably, the step (a) is carried out in the presence of a standard chemical substance having a known action on the biological sample, and in the presence of a subject chemical substance, respectively, and the step (f) is carried out with concentrations of the standard chemical substance and the subject chemical substance being changed, respectively, and the method further comprises comparing changes in the physicochemical characteristic in the presence of the standard chemical substance obtained in the step (g) with a change in the physicochemical characteristic in the presence of the subject chemical substance obtained in the step (g), and characterizing an action of the subject chemical substance on the biological sample.

According to one aspect of the present invention, an apparatus for measuring an action of a subject chemical substance on a biological sample, comprises a reaction system for measuring a physicochemical characteristic of the biological sample, comprising the above-described device, means for recording a physiochemical signal emitted from the biological sample of interest as a time-series signal value, means for sampling the time-series signal value to obtain a plurality of groups of extracted data consisting of a plurality of values, and calculating a standard deviation of each of the plurality of groups, means for calculating an average of each of the standard deviations, and means for detecting a change in the physiochemical characteristic of the biological sample based on the average.

In one aspect of the present invention, an apparatus for measuring an action of a subject chemical substance on a biological sample, comprises a reaction system for measuring a physicochemical characteristic of the biological sample, comprising the above-described device, means for recording a physiochemical signal emitted from the biological sample of interest as a time-series signal value, means for sampling the time-series signal value to obtain a plurality of groups of extracted data consisting of a plurality of values, and calculating a standard deviation of each of the plurality of groups, means for dividing the standard deviations into a plurality of classes having a predetermined size of standard deviation as a unit, and obtaining a distribution indicating physicochemical characteristics of the plurality of groups of extracted data belonging to the classes, means for approximating the distribution to a normal distribution, means for calculating an average and a half-width of the resultant normal distribution, and means for detecting a change in the physicochemical characteristic of the biological sample based on the average and half-width.

In one aspect of the present invention, an apparatus for measuring an action of a subject chemical substance on a biological sample, comprises a reaction system for measuring a physicochemical characteristic of the biological sample, comprising the above-described device, means for recording a physiochemical signal emitted from the biological sample of interest as a time-series signal value, means for sampling the time-series signal value to obtain a plurality of groups of extracted data consisting of a plurality of values, and calculating a standard deviation of each of the plurality of groups, means for dividing the standard deviations into a plurality of classes having a predetermined size of standard deviation as a unit, and obtaining a distribution indicating physicochemical characteristics of the plurality of groups of extracted data belonging to the classes, means for approximating the distribution by curvilinear approximating analysis selected from the group consisting of exponential decreasing analysis, exponential increasing analysis, Gaussian distribution, Lorentz distribution, σ analysis, multiple peak analysis, and nonlinear analysis, and means for detecting a change in the physicochemical characteristic of the biological sample based on gradients before and after a peak on the obtained approximated curve.

In one aspect of the present invention, an apparatus for measuring an action of a subject chemical substance on a biological sample, comprises a reaction system for measuring a physicochemical characteristic of the biological sample, comprising the above-described device, means for recording a physiochemical signal emitted from the biological sample of interest as a time-series signal value, means for sampling the time-series signal value to obtain a plurality of groups of extracted data consisting of a plurality of values, and calculating a standard deviation of each of the plurality of groups, means for sampling the resultant standard deviations to obtain a plurality of groups of extracted standard deviations consisting of a plurality of values, and calculating an average of each of the plurality of groups of extracted standard deviations, and means for obtaining an index value detecting a change in the physicochemical characteristic of the biological sample based on a time of occurrence of the time-series signal value when the average reaches a predetermined threshold.

In one aspect of the present invention, an apparatus for screening drugs at high speed, comprises at least one reaction system for measuring a physicochemical characteristic of a biological sample of interest, comprising the above-described device, and means for detecting a change in the physicochemical characteristic of the biological sample of interest. The reaction system comprises a reference electrode and a measuring electrode, and an arrangement and an environment or a characteristic of the reference electrode and the measuring electrode are adapted to characterize a change in the physiochemical characteristic of the biological sample of interest.

In the device of the present invention, an electrode is provided on a porous film by a technique, such as sputtering, so that an electrode material impregnates the porous film deeply and is present in the vicinity of a biological sample. Therefore, the device can detect a physicochemical activity of a cell in an efficient and highly sensitive manner. Moreover, in the device of the present invention, extracellular potential is measured. Therefore, it is not necessary to fill space adjacent to a side of the porous film, on which a measuring electrode is provided, with electrolyte, like an intracellular recording method. In the device of the present invention, only a small amount of electrolyte (typically, Krebs ringer solution) is present in such a space. The amount of such electrolyte is no more than about 1-10 μl including electrolyte contained in the porous film. In contrast, in the device disclosed in WO 01/25769 A2, electric current is measured between two domains separated by a cell membrane, so that it is necessary to fill a suction system with solution. In other words, the device of the present invention does not require a gigaseal between a cell and an electrode.

Further, whereas a device produced by micromachining a semiconductor substrate has a difficulty in liquid exchange, the device of the present invention employs a porous material, such as a hollow fiber membrane, typically used for filtration. Therefore, it is possible to easily exchange fluid by suction. Specifically, Isopore (made of polyethyleneterephthalate: manufactured by Millipore), Omnipore (polytetrafluoroethylene: manufactured by Millipore), or the like may be used as a porous film in the present invention.

The method and apparatus of the present invention for measuring a physicochemical change emitted by a cell and a tissue can extract and measure a significant signal due to the opening or closing of an ion channel from an extracellularly recorded signal, which cannot be conventionally detected. Particularly, the present invention provides a method for measuring and categorizing an ion channel activity of a whole cell, in which a simple device, which does not require a specialized control apparatus, is employed and the cell can be easily measured in a short time, and in which since no chemical substance is employed, it is not necessary to consider any side effect or any change in fluorescence sensitivity over time; and high-speed drug screening using the method.

The method of the present invention for measuring a physicochemical change emitted by a cell and a tissue can be applied to drug screening. For example, in the case of measurement of an electrophysiological cellular function, a significant signal is extracted from a captured signal as a digital signal, and measured and categorized, so that the present invention is very useful for high-speed drug screening applications.

These and other advantages of the present invention will become apparent to those skilled in the art upon reading and understanding the following detailed description with reference to the accompanying figures.

BRIEF DESCRIPTION OF THE DRAWINGS

FIGS. 7(A) and 7(B) are schematic cross-sectional views of the device shown in FIG. 3.

FIG. 8 is a schematic diagram showing a configuration of an apparatus according to the present invention.

Figure 1:
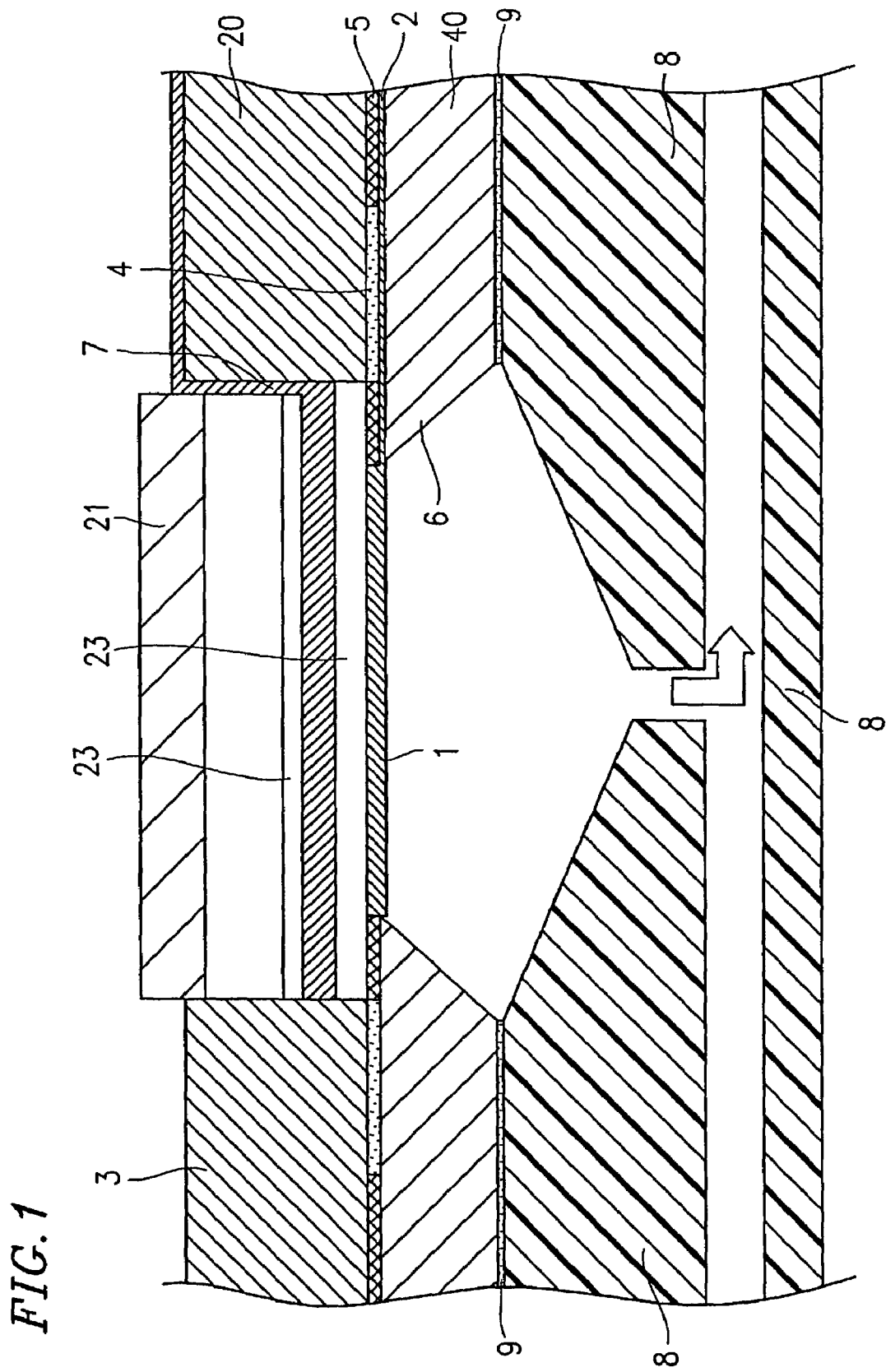
FIG. 1 is a schematic cross-sectional view of an exemplary device according to the present invention for detecting a physicochemical change in a biological sample.

Note that reference numerals used in FIGS. 1-14 indicate the following members: 1 measuring electrode; 2 conductor; 3 cell isolation portion; 4 adhesive layer; 5 porous film; 6 support substrate; 7 reference electrode; 8 suction line attachment; 9 support substrate-suction line attachment adhesive layer; 12 conductor; 21 cover; 23 culture medium; 25 cell; 101 signal source; 102 unit standard deviation calculation section; 103 normal distribution approximation section; 104 trigger signal generating section; 105 average calculation section; 106 average/half-width calculation section; 107 signal adding up section; 108 activity calculation section; 109 activity categorization section; 110 data displaying section; 111 sample number categorization section.

DESCRIPTION OF THE PREFERRED EMBODIMENTS

Hereinafter, the present invention will be described by way of illustrative examples with reference to the accompanying drawings.

EXAMPLE 1

FIG. 1 is a schematic cross-sectional view of an exemplary device according to the present invention for detecting physicochemical changes in a biological sample. A measuring electrode 1 for detecting physicochemical changes in a biological sample (typically, cells) is provided on a rear side of a porous film 5, and a conductor 2 is drawn from the measuring electrode 1.

Typically, the porous film 5 is made of, but not limited to, nylon mesh. The material for the porous film 5 further includes cellulose-mixed ester, hydrophilic polyvinylidendifluoride, hydrophobic polyvinylidendifluoride, polytetrafluoroethylene, polycarbonate, polypropylene, and polyethyleneterephthalate. The porous film 5 in the present invention typically has a hole diameter of about 1 to about 1000 μm and a thickness of about 1 to about 10000 μm. A representative size thereof is a hole diameter of about 5 μm and a thickness of about 10 μm.

Note that, as described below, the thickness of the measuring electrode 1 can be changed by adjusting the time of sputtering when the measuring electrode 1 is formed. Therefore, the film material having a thickness of 100 μm or more can be preferably employed.

The measuring electrode 1 and the conductor 2 are formed representatively by sputtering a conductive material (representatively, gold). A technique for sputtering a conductive material is known to those skilled in the art. For example, gold is employed to do sputtering. Plasma is generated using high frequency wave between electrodes in the presence of inert gas, such as argon, and under low vacuum. Ion energy impinges on gold on a negative electrode, so that the scattered gold forms an electrode on a porous film disposed on an opposing positive electrode. Alternatively, vacuum deposition or the like may be used to form an electrode and a conductor. An electrode and a conductor can also be formed by printing.

The conductor 2 is formed as follows: the porous film 5 is covered with a mask (not shown) before patterning so that conductive material is prevented from entering deeply into the porous film 5. In contrast, the measuring electrode 1 is preferably formed by sputtering without a mask so that an electrode material is permitted to enter deeply into the porous film 5. The measuring electrode 1 formed by sputtering is typically in the shape of a circular plate, but may be in any shape depending on the subject to be measured. The measuring electrode 1 may have any size depending on the subject to be measured. Typically, the measuring electrode 1 has a surface area corresponding to the horizontal cross-sectional area of a chamber defined by a cell isolation portion 3. A subject sample is accommodated in the chamber.

Next, the porous film 5 provided with the measuring electrode 1 and the conductor 2 is fixed on a support substrate 6. Thereafter, the cell isolation portion 3 is attached to a surface of the porous film 5 with an adhesive by applying pressure. The adhesive forms an adhesive layer 4. The adhesive layer 4 prevents cell culture medium or measurement solution 23 from permeating out through the porous film 5. The cell isolation portion 3 defines the chamber for accommodating the cell culture medium or measurement solution 23. Note that a member indicated by reference numeral 21 is a cover for preventing evaporation of the cell culture medium or measurement solution 23 in the chamber. The cover 21 is optionally, but not necessarily, employed.

A suction line attachment 8 constituting a suction line is attached to the support substrate 6 via a support substrate-suction line attachment adhesive layer 9. About 50 μl of culture medium is provided on the porous film 5 while a little amount of culture medium is present under the porous film 5. The volume ratio of the culture medium on the porous film 5 to the culture medium under the porous film 5 is typically about 50:1 or more. The volume of the chamber occupied by the culture medium on the porous film 5 is herein referred to as a "domain in which a reference electrode is provided". The volume of the chamber occupied by the culture medium under the porous film 5 is herein referred to as a "domain in which a measuring electrode is provided".

Figure 2:
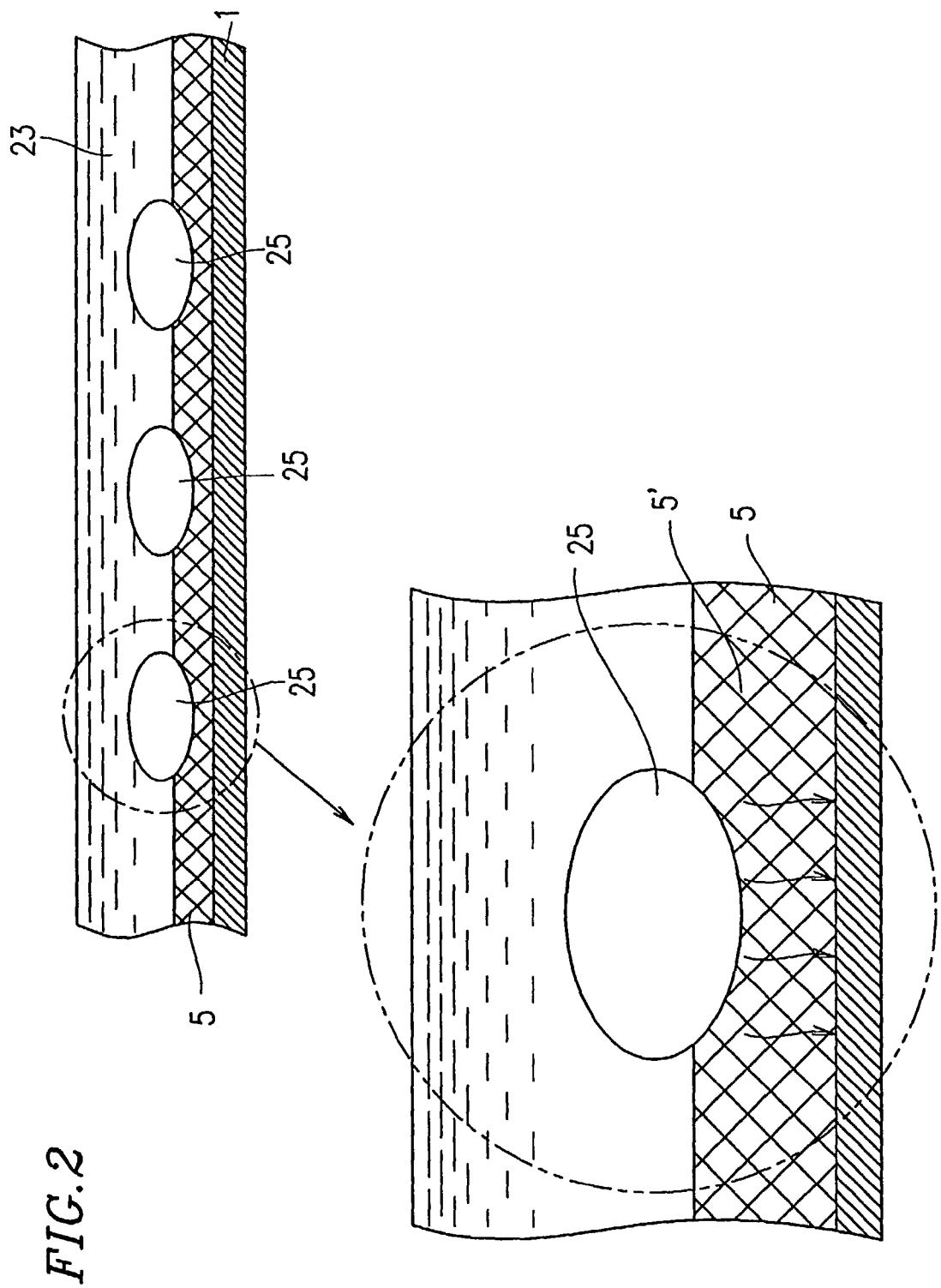
FIG. 2 is a schematic diagram showing the principle of the method of the present invention for detecting a physicochemical change in a biological sample.

Referring to FIG. 2, the thickness of the porous film 5 is selected so that the measuring electrode 1 disposed under porous film 5 contacts or is very close to a biological sample. Typically, the distance between the biological sample and the measuring electrode 1 is within about 50 μm. Preferably, the measuring electrode 1 contacts cells 25. Representatively, in measurement, the suction line provided under the support substrate 6 shown in FIG. 1 suctions the cells 25 so as to bring the cells 25 into intimate contact with the measuring electrode 1 so that physicochemical changes in the cells 25 can be detected with high sensitivity. A diagram at a lower part of FIG. 2 is an enlarged view of the vicinity of the cell 25, schematically showing with arrows that a physicochemical signal emitted by the cell 25 is transferred to the measuring electrode 1.

The porous film 5 makes it easy to handle solution containing a candidate compound for a drug to be tested. Specifically, all subject solution present on the film 5 can be exchanged in a short time by suctioning through the suction line attachment included in the device (indicated by an arrow at the middle of FIG. 1).

EXAMPLE 2

Figure 3:
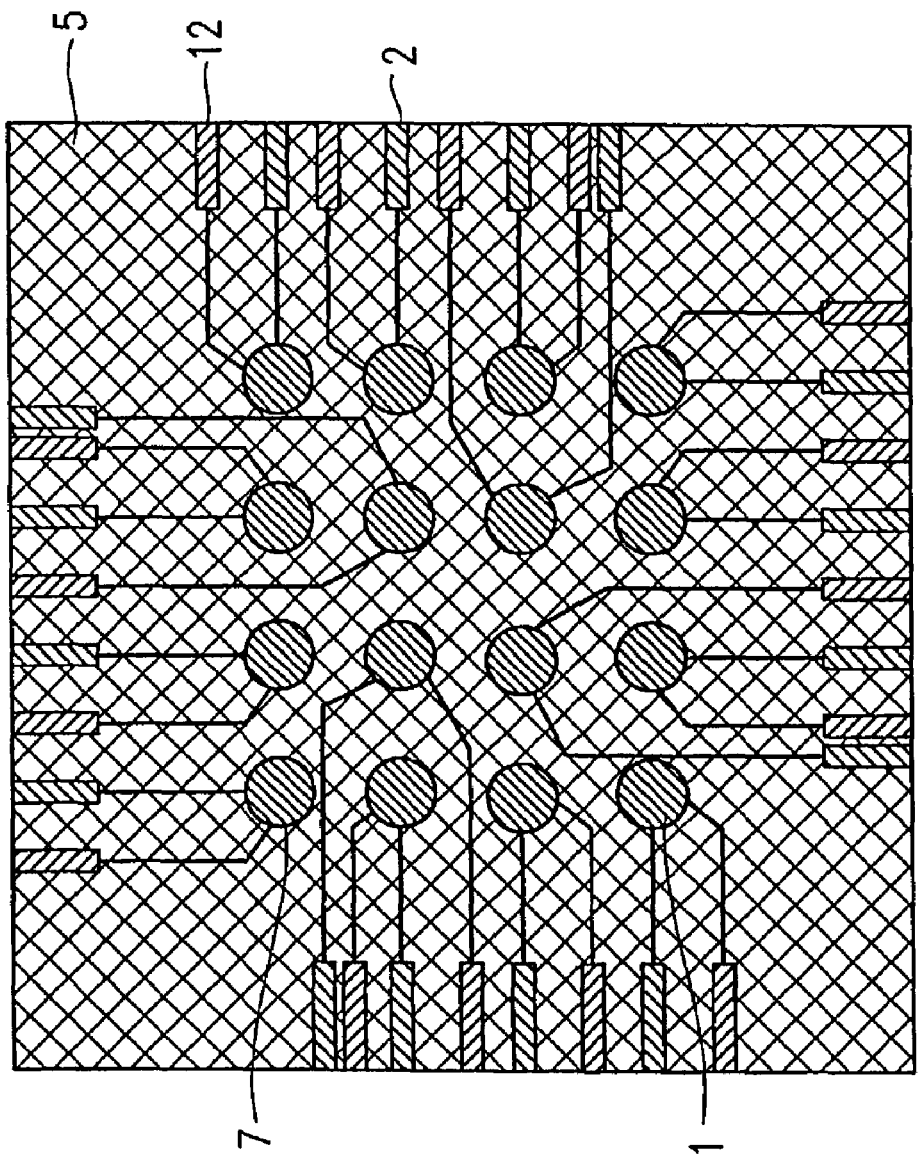
FIG. 3 is a schematic plan view of another exemplary device according to the present invention for detecting physicochemical changes emitted by a biological sample.

FIG. 3 is a schematic plan view of another exemplary device according to the present invention for detecting physicochemical changes emitted by a biological sample. The device comprises 16 measuring electrodes 1, each of which has a diameter of 2 mm, are spaced at intervals of 1 mm and arranged in a matrix. FIG. 3 is an imaginary diagram of the device viewed over the top. In FIG. 3, reference electrodes 7 and conductors 12 connected thereto are disposed on the inner walls of chambers defined by a cell isolation portion 3 (not shown), which is typically transparent, and a surface of the cell isolation portion 3, respectively. A biological sample is accommodated by the chambers. Measuring electrodes 1 and the conductors 2 connected thereto are provided on the rear side of the porous film 5. In the example of FIG. 3, the 16 measuring electrodes 1 are substantially in the shape of a circle. However, any number of measuring electrodes having any shape and area can be provided and spaced at appropriate intervals in the device. Typically, the area of the measuring electrode is about 1 μm$^2$ to 1 cm$^2$ and the shape thereof is substantially circular or a rectangular. The measuring electrodes are spaced at intervals of about 10 to about 10000 μm and disposed in a matrix.

Figure 4A:
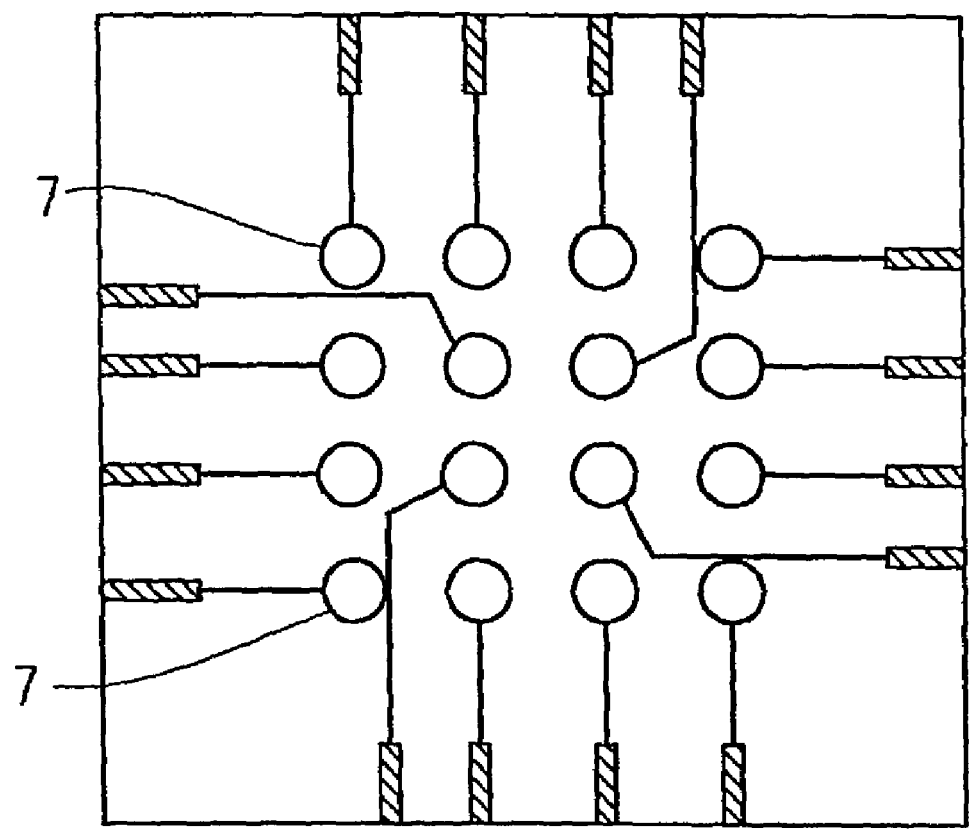
FIGS. 4(A) and 4(B) are a schematic plan view and cross-sectional view, respectively, of a structure on the porous film 5 constituting the device shown in FIG. 3.
Figure 4B:
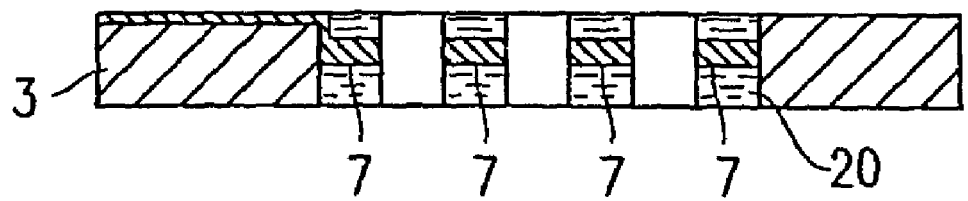

FIGS. 4(A) and 4(B) are a schematic plan view and cross-sectional view, respectively, of a structure on the porous film 5 constituting the device shown in FIG. 3. As shown in FIG. 4(A), an annular reference electrode 7 is provided on the inner wall of the chamber defined by the cell isolation portion 3, and is connected to a conductor extending to a side of a substrate.

Figure 5A:
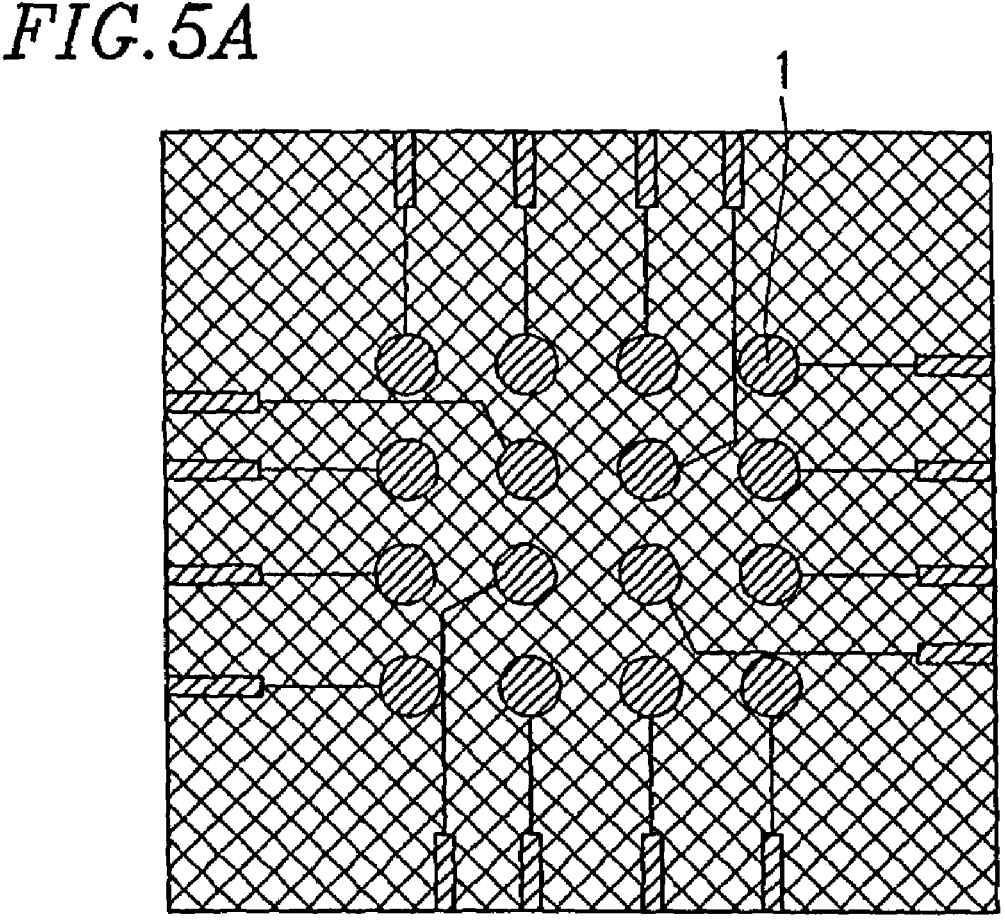
FIGS. 5(A) and 5(B) are a schematic plan view and cross-sectional view, respectively, of a structure under the porous film 5 constituting the device shown in FIG. 3.
Figure 5B:
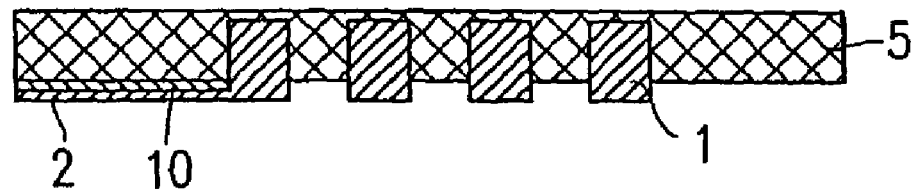

FIGS. 5(A) and 5(B) are a schematic plan view and cross-sectional view, respectively, of a structure under the porous film 5 constituting the device shown in FIG. 3. As shown in FIG. 5(B), the measuring electrode 1 hatched by slanting lines is formed by sputtering a conductive material which impregnates the porous film 5. The conductor 2 is formed by sputtering a conductive material where a mask layer 10 is provided on the film 5 so that the conductive material is prevented from entering deeply into the film 5.

Figure 6:
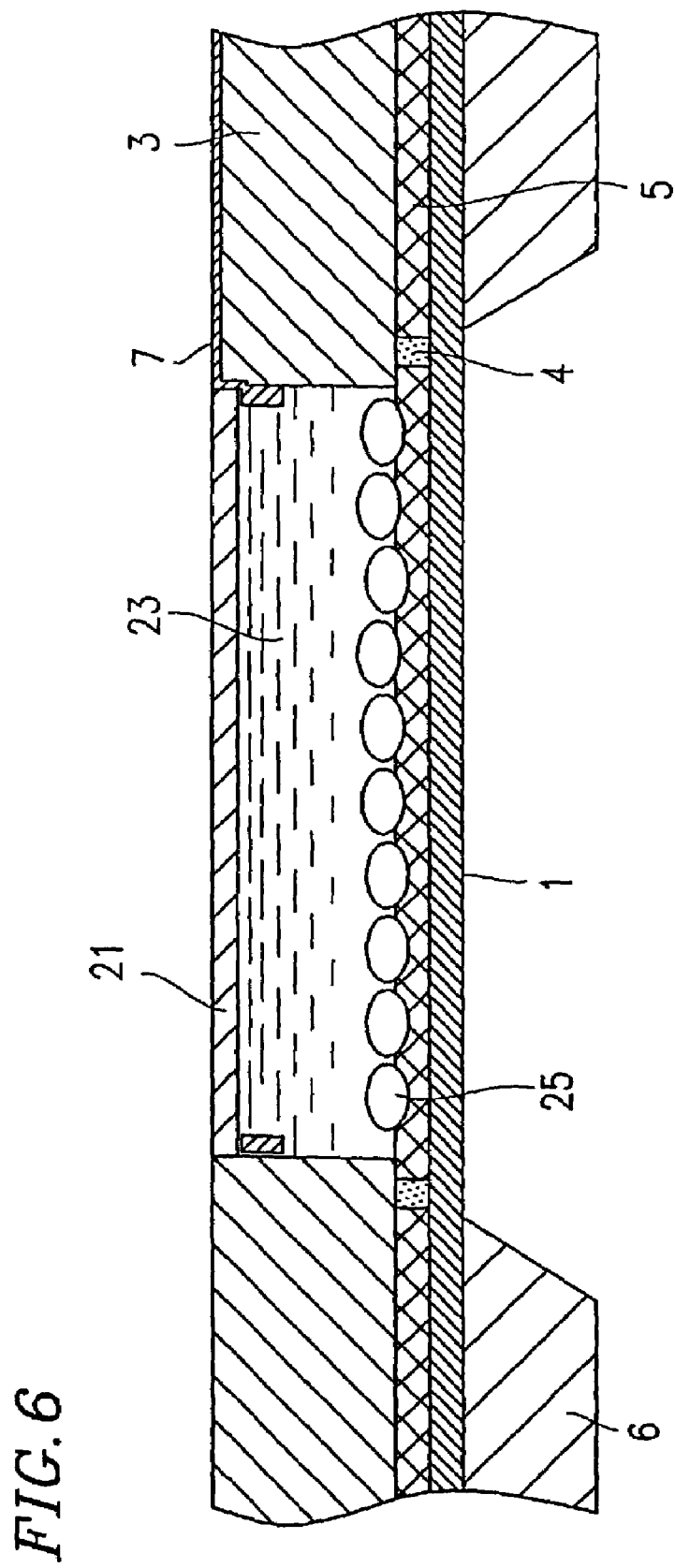
FIG. 6 is a schematic cross-sectional view of the device shown in FIG. 3.

FIGS. 6 and 7(A) and 7(B) are schematic cross-sectional views of the device shown in FIG. 3. FIG. 6 shows the structure of the reference electrode 7 in more detail. FIGS. 7(A) and 7(B) shows the structure of the measuring electrode 1 in more detail. FIG. 7(A) is a schematic cross-sectional view of the structure of the measuring electrode 1. FIG. 7(B) is a schematic plan view of an arrangement of the 16 measuring electrodes 1 and the conductors 2 connected thereto in the device. A cross-section of a portion indicated by X in FIG. 7(B) is shown in FIG. 7(A).

As shown in FIG. 6, the reference electrode 7 has a substantially annular structure provided on the inner wall of the chamber defined by the cell isolation portion 3. The reference electrode 7 is connected to and drawn by the conductor 2 provided on the cell isolation portion 3. The reference electrode 7 provides a reference potential for detecting physicochemical changes of a cell 25 indicated by an ellipse in FIG. 7(B). For example, the reference electrode 7 is made of Ag—AgCl. As shown in FIG. 7(A), the measuring electrode 1 is formed by causing an electrode material to enter into the porous film 5 so that the measuring electrode 1 is disposed in the vicinity of a cell to be measured. The conductor 2 connected to the measuring electrode 1 is disposed in such a manner that the conductor 2 and the porous film 5 sandwich the mask layer 10.

EXAMPLE 3

FIG. 8 is a conceptual diagram showing a configuration of an apparatus comprising the above-described device for detecting physicochemical changes emitted by a biological sample, which is configured to measure and extract the ion channel activity of the biological sample. The apparatus comprises a measurement section (signal source) 101 comprising a device for detecting physicochemical changes emitted by the biological sample and measuring an action potential generated by a neuron, a unit standard deviation calculation section 102 for sampling a signal from the measurement section 101 and calculating the standard deviation of the signal, an average calculation section 105 for calculating the average of the obtained standard deviation, an activity calculation section 108 for calculating the ion channel activity of a cell from the average of the standard deviation output by the average calculation section 105, and a data displaying section 110 for displaying the calculated activity. Communications between each section are indicated by a dashed line or a solid line in FIG. 8. Note that the unit standard deviation calculation section 102, and the average calculation section 105, and the activity calculation section 108 may be representatively software programs which are recorded in a hard disk in a computer. The data displaying section 110 may be a CRT.

Note that reference numerals 103, 104, 106 and 109 in FIG. 8 indicate a normal distribution approximation section, a stimulus generation section, an average/half-width calculation section and an activity categorization section described below, respectively.

The measurement section (signal source) 101 comprises the sensor substrate shown in FIG. 3. The apparatus having the configuration shown in FIG. 8 was used to measure an action of a neuron to the chemical substance Carbachol, where the neuron was prepared from *Lymnaea stagnail*. Carbachol is a chemical substance known as an analog of the neurotransmitter Acetylcholine. Carbachol (manufactured by Sigma) was dissolved in artificial cerebrospinal fluid to concentrations of 0, 0.1, 0.3, 1, 3, 10, 30 and 100 μM. The solutions having these concentrations were used to measure an electrical signal emitted by the neuron. For each Carbachol concentration, time-series data for 10 seconds was obtained from the measurement section (signal source) 101 comprising the sensor substrate, and was sampled at intervals of 100 miliseconds, and the standard deviation of the sampling data was calculated. The average of the standard deviation was plotted in FIG. 12.

Figure 12:
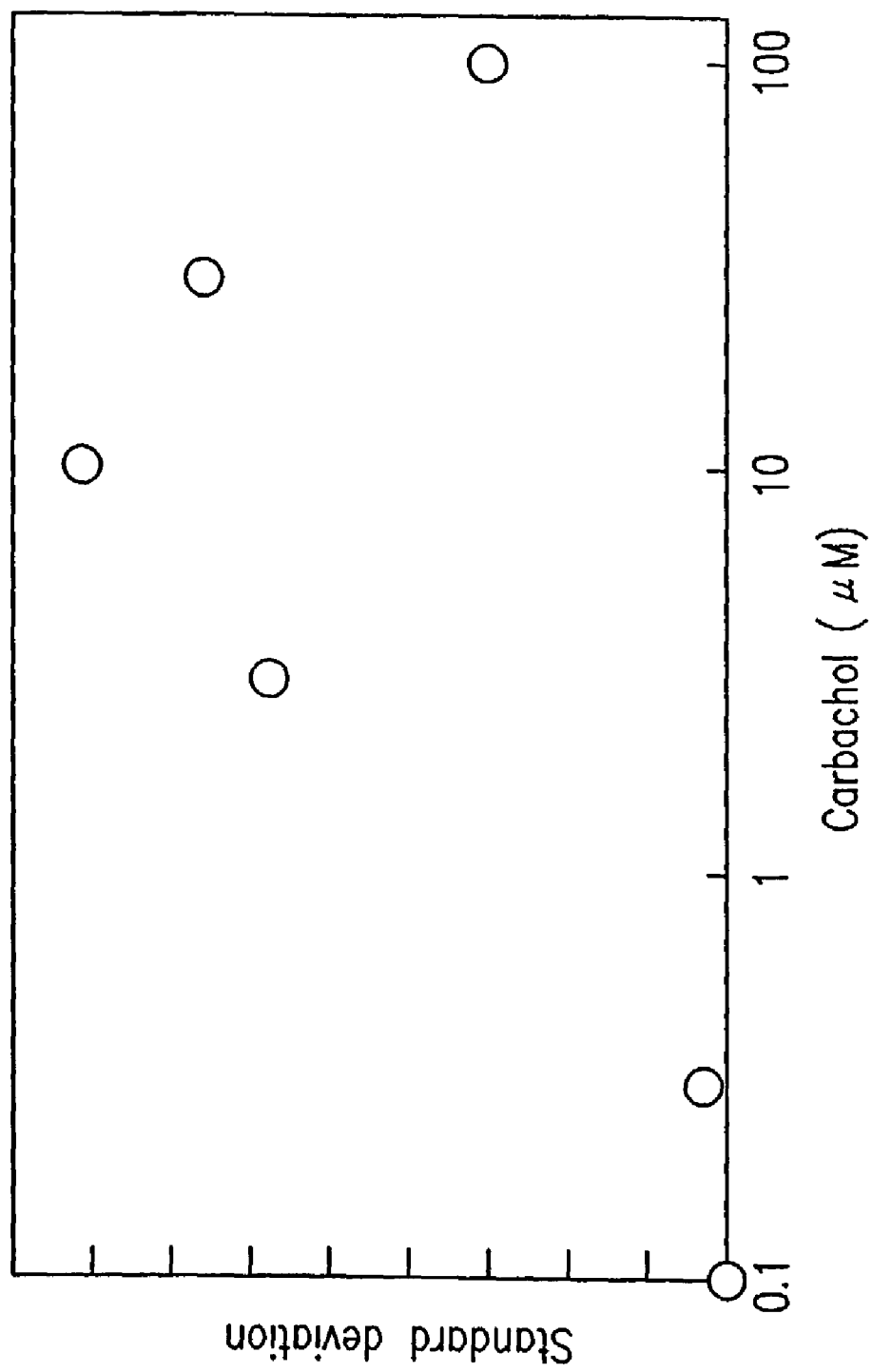
FIG. 12 is a diagram showing a concentration-dependent reaction of a *Lymnaea stagnail* neuron to Carbachol, which was measured by the apparatus of the present invention.

As can be seen from FIG. 12, the greater the Carbachol concentration, the greater the average of the standard deviation every 100 miliseconds. This result indicates that the ion channel of a *Lymnaea stagnail* neuron was activated depending on the Carbachol concentration. Moreover, it is possible to deduce the total activities of all ion channels of a neuron.

EXAMPLE 4

Figure 9:
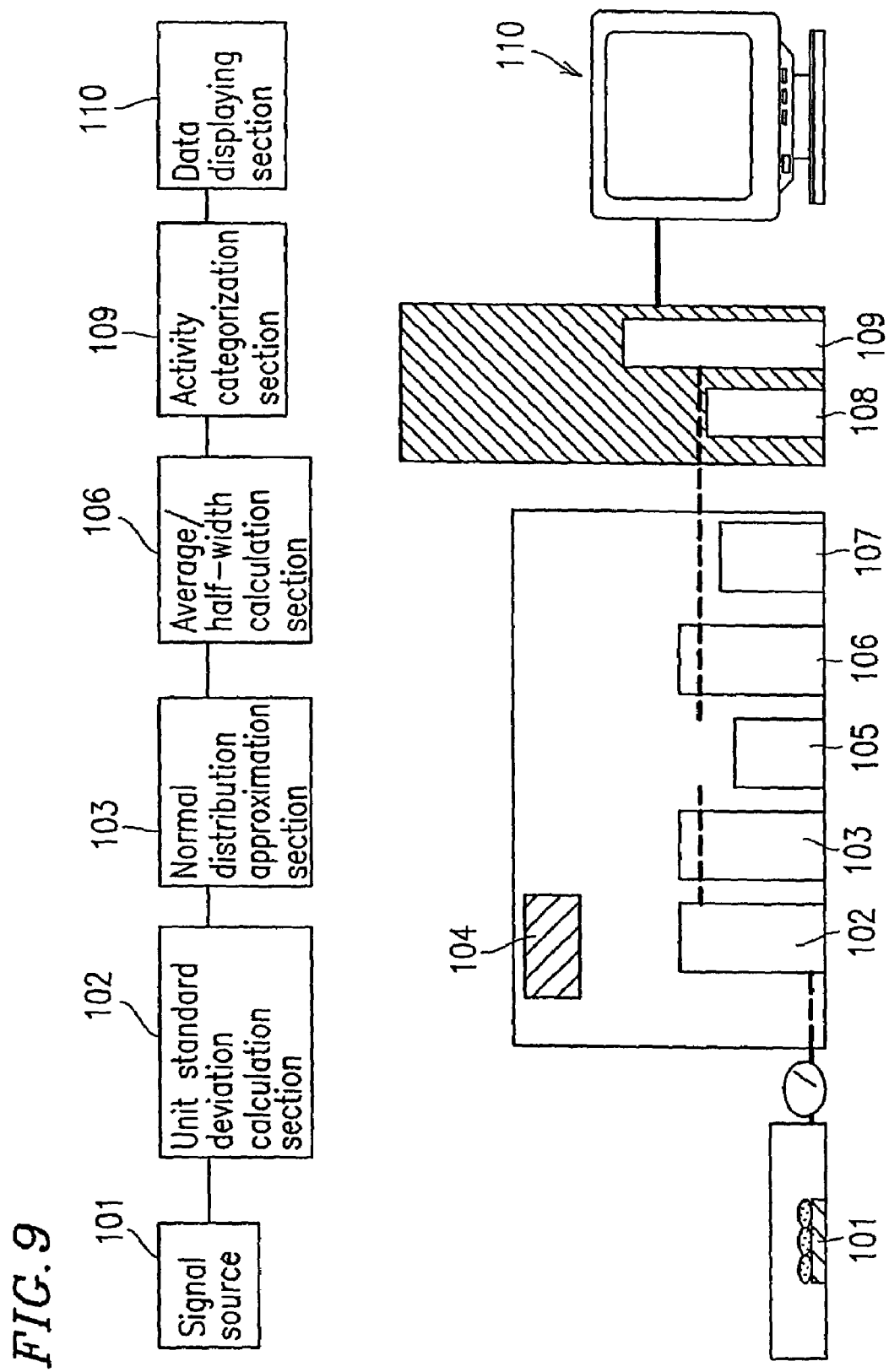
FIG. 9 is a schematic diagram showing a configuration of a variation of the apparatus of the present invention.

FIG. 9 is a conceptual diagram showing a configuration of an apparatus comprising the above-described device for detecting physicochemical changes emitted by a biological sample, which is configured to measure and extract the ion channel activity of the biological sample. The apparatus is the same as the apparatus of FIG. 8, except that the normal distribution approximation section 103, the average/half-width calculation section 106 and the activity categorization section 109 are employed in place of the average calculation section 105 and the activity calculation section 108. Communications between each section are indicated by a dashed line or a solid line in FIG. 9.

The normal distribution approximation section 103 divides a plurality of standard deviation values obtained by the unit standard deviation calculation section 102 into a plurality of classes having a predetermined width of standard deviation as a unit, plots the standard deviation values where the X axis represents the class and the Y axis represents the number of standard deviation values belonging to the class, and approximates the obtained graph to a normal distribution. The average/half-width calculation section 106 calculates the average and half-width of the resultant normal distribution. The activity categorization section 109 categorizes an ion channel activity based on the obtained average and half-width. Note that similar to the apparatus of FIG. 8, the unit standard deviation calculation section 102, the normal distribution approximation section 103, the average/half-width calculation section 106 and the activity categorization section 109 may be representatively software programs which are recorded in a hard disk of a computer. The data displaying section 110 may be a CRT.

The measurement section (signal source) 101 comprises the sensor substrate shown in FIG. 3. The apparatus having the configuration shown in FIG. 9 was used to measure an action of a neuron to Carbachol, where the neuron was prepared from *Lymnaea stagnail*.

Before and after 50 µM-concentration Carbachol is applied to a *Lymnaea stagnail* neuron, signals were obtained from the measurement section (signal source) 101, and the standard deviation of the signals was calculated in a manner similar to that of Example 1. The normal distribution approximation section 103 plotted the standard deviations into a graph which is shown in FIG. 13.

Figure 13:
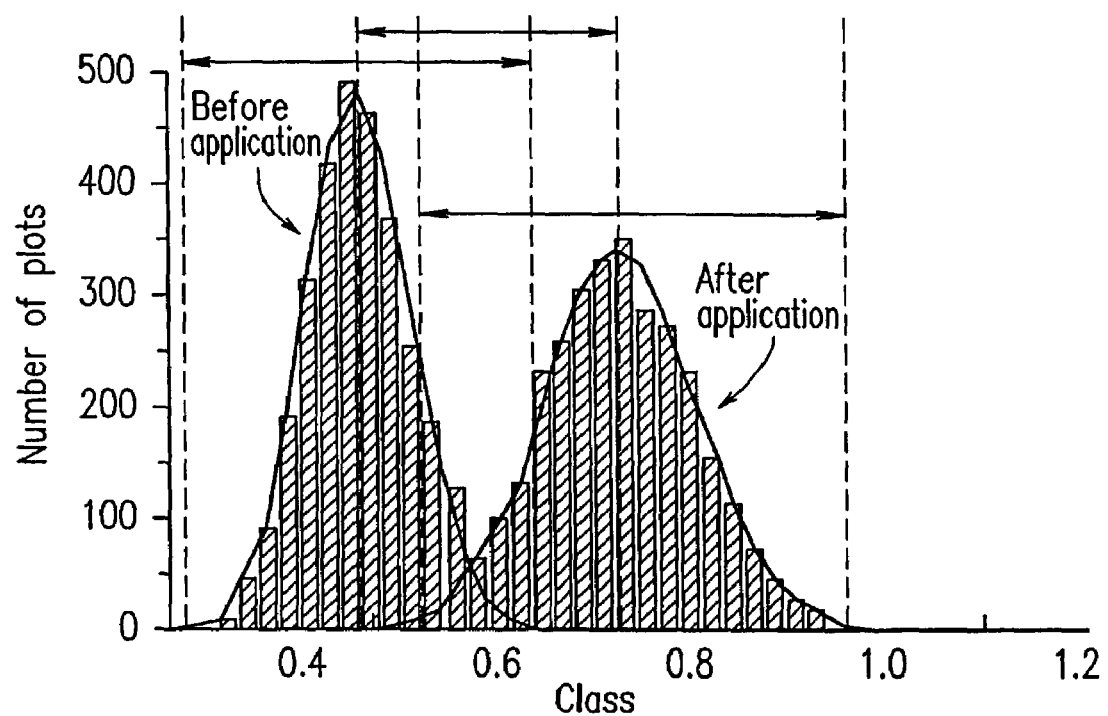
FIG. 13 is a diagram showing a result of measuring a *Lymnaea stagnail* neuron before and after applying Carbachol thereto, which was measured by the apparatus of the present invention.

FIG. 13 shows a histogram of standard deviation values calculated every 5 miliseconds from time-series data of an electrical signal for 10 seconds before applying Carbachol and a histogram of standard deviation values calculated every 5 miliseconds from time-series data of an electrical signal for 10 seconds after applying Carbachol. As shown in FIG. 13, the histograms before and after applying Carbachol approximated normal distributions. The average and half-width of the resultant normal distribution graph are 0.478 and 0.109, respectively, before the application, and 0.703 and 0.175, respectively, after the application. Thus, it is confirmed that the average of the standard deviation every 5 miliseconds was increased from before to after applying Carbachol. This is because applying Carbachol activates an ion channel of a *Lymnaea stagnail* neuron and the opening or closing of the activated ion channel causes a change in action potential which is reflected in the result shown in FIG. 13.

Figure 14:
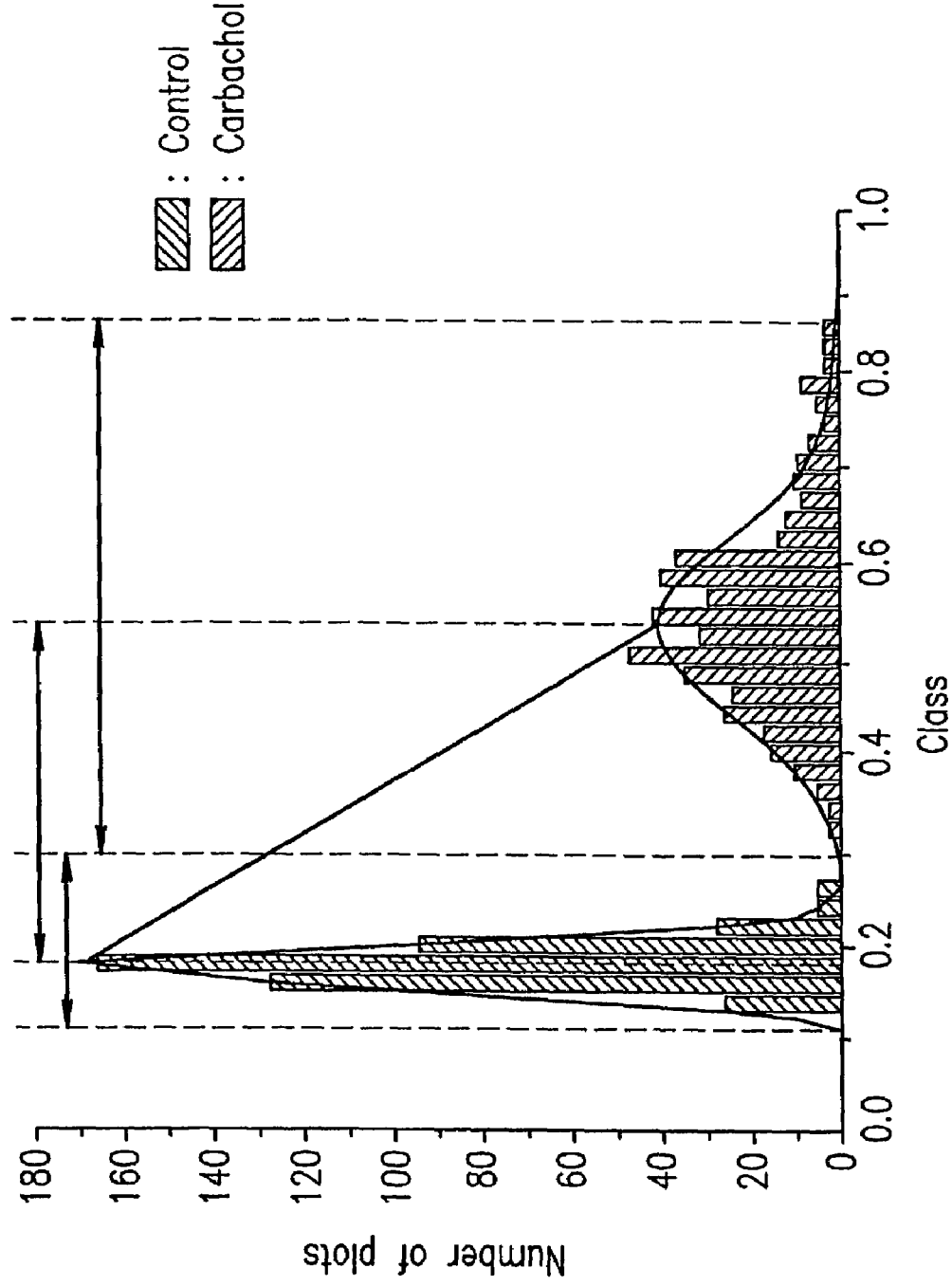
FIG. 14 is a diagram showing a result of measuring a *Lymnaea stagnail* neuron before and after applying Carbachol thereto, which was measured by a conventional intracellular recording method.

FIG. 14 shows a histogram of standard deviation values every 5 miliseconds where data obtained by a conventional intracellular recording method was subjected to signal processing as described above. As can be seen from FIG. 14, the measurement result of the extracellular recording method is similar to that of the intracellular recording method.

As described above, according to the technique of the present invention, cellular activities associated with the opening or closing of ion channels and changes therein can be measured without conventional intracellular recording methods. Therefore, the present invention makes possible qualitative or quantitative categorization of the action or effect of a drug by measurement of ion channel activities and comparison of the absolute values of or an increase or decrease in ion channel activities before and after applying a drug into a cell or depending on the amount of the drug.

EXAMPLE 5

Figure 15:
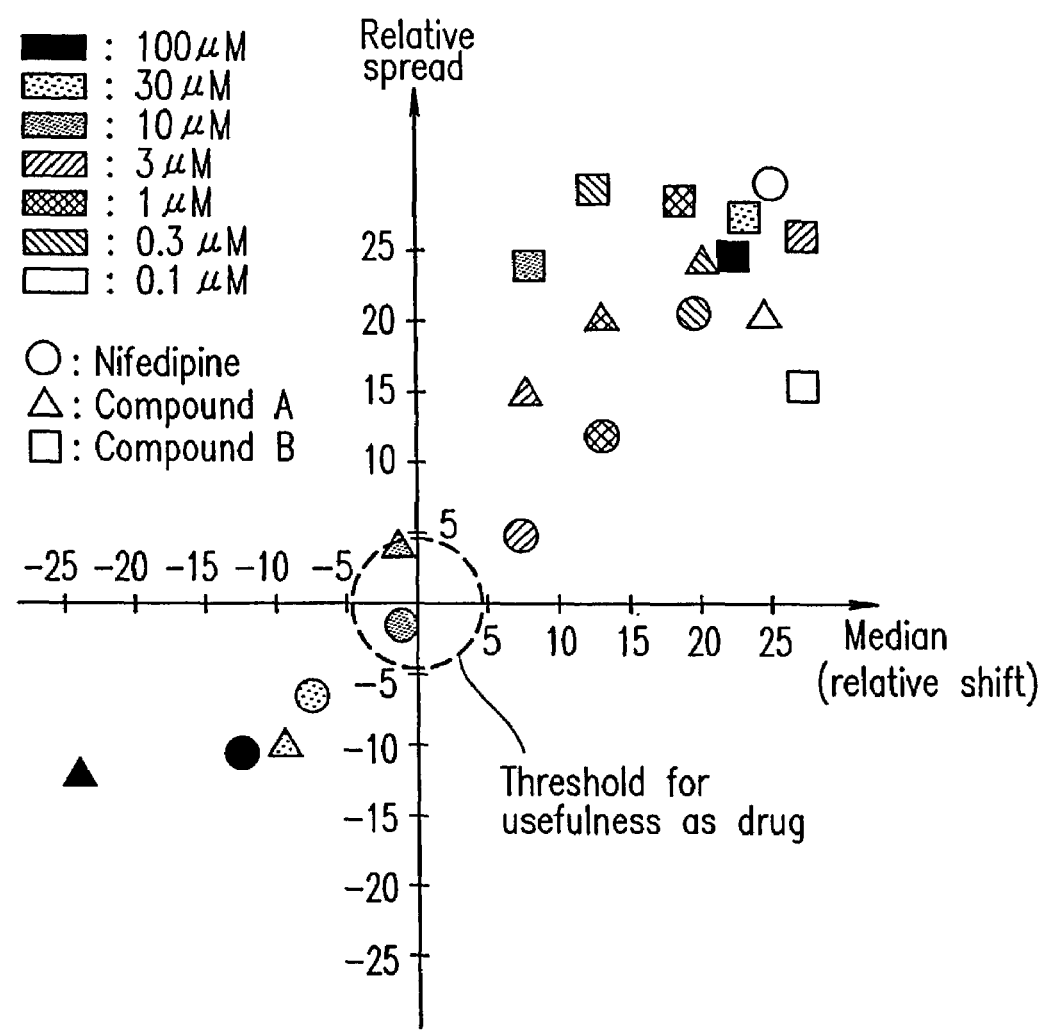
FIG. 15 is a diagram showing a method according to the present invention for categorizing an effect of a drug.

Intracellular recording studies and the like have confirmed that the activity of the Ca ion channel of smooth muscle cells is inhibited by nifedipine in a concentration-dependent manner when the cell is stimulated by 10 µM norepinephrine. In data obtained by intracellular recording, nifedipine inhibition is represented and plotted by two variables, i.e., a deviation of the average of the normal distribution of standard deviations from a reference value (relative shift value) and a deviation of the half-width thereof from a reference value (relative spread) in FIG. 15. In FIG. 15, circles indicate nifedipine having a changing concentration (0.03 to 30 µM).

The effect of nifedipine on the Ca ion channel, which was recorded by the intracellular recording method, was used as database to categorize the effects of two drugs A and B for inhibiting the Ca ion channel, which were recorded by the same extracellular recording method as that of Example 4. The ion channel activity of a cell was measured by the same method as that of Example 2 while the concentrations of the drugs A and B were changed in the range of 0.03 to 30 µM. Similar to nifedipine, the resultant effect was represented and plotted by two variables, i.e., a deviation of the average of the normal distribution of standard deviations from a reference value (relative shift) and a deviation of the half-width thereof from a reference value (relative spread) in FIG. 15. In FIG. 15, triangles indicate compound A, while squares indicate compound B. As shown in FIG. 15, compound A (triangle) behaves in a concentration-dependent manner in substantially the same manner as that of nifedipine (circles) within the above-described concentration range. Therefore, compound A was inferred to be a Ca ion channel inhibitor similar to nifedipine. In contrast, compound B has substantially no changes in the above-described relative shift and relative spread, so that compound B is highly probably not a Ca ion channel blocker which is present in the smooth muscle cell.

As described above, the method of the present invention makes it possible to deduce the effect of an unknown drug. Moreover, for example, drugs may be assessed using a threshold indicated by a dashed circle indicating that the above-described relative shift and relative spread are each within about 5% as shown in FIG. 15 (specifically, a concentration giving a measured value to be plotted within the circle does not have any pharmaceutical effect, while a concentration giving a measured value not to be plotted within the circle has a pharmaceutical effect), thereby making it possible to screen drugs efficiently.

In the above-described examples, a deviation of the average of a normal distribution from a reference value and a deviation of the half-width thereof from a reference value are employed. Alternatively, corresponding parameters of standard deviation and variance may be used to estimate the effect of a drug.

As described above, in the present invention, the arrangement and environment or characteristics of the reference electrode and the measuring electrode are adapted to characterize a change in electrical characteristics of a biological sample. Therefore, an electrical change in a biological sample can be measured without forming a high resistance seal (gigaseal) between a cell (or a tissue) and a measuring device. Further, in the present invention, the step of detecting a change in electrical characteristics of a biological sample representatively processes a digital signal (predetermined time-series data) captured at a constant sampling rate, so that a significant signal representing the opening or closing of an ion channel can be extracted from noise, and measured and categorized.

Figure 10:
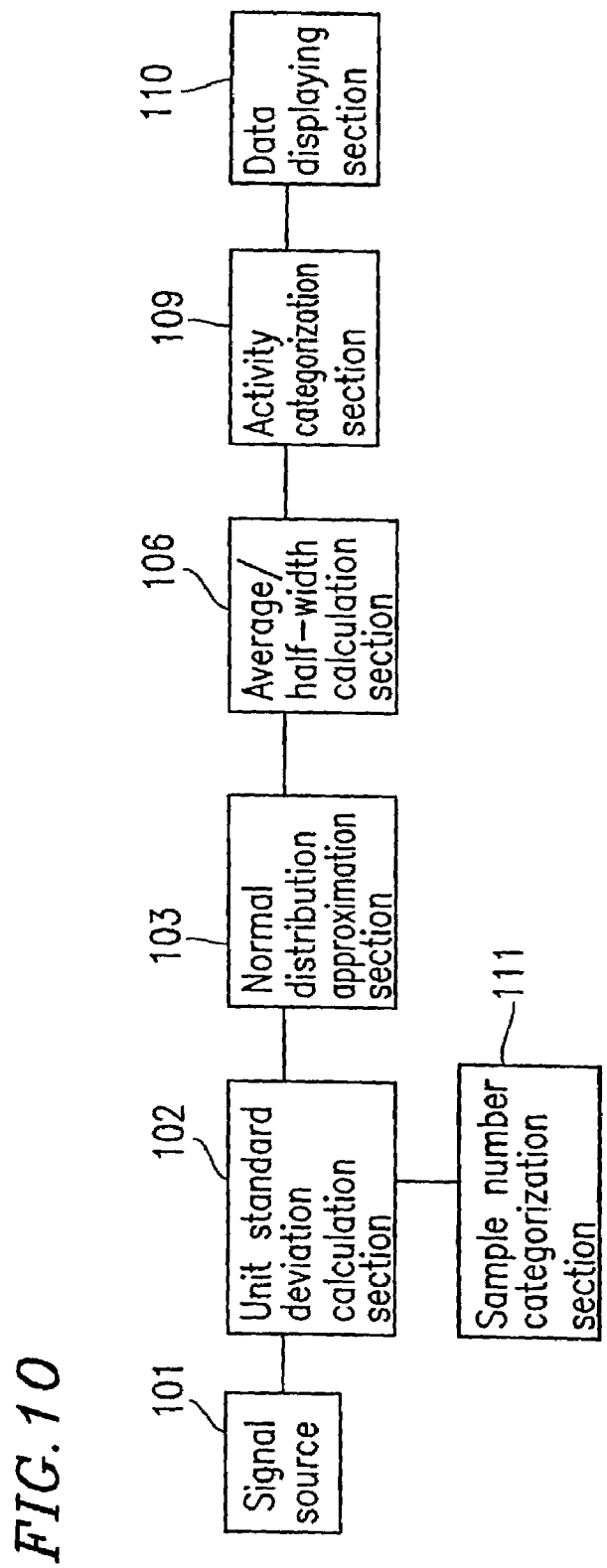
FIG. 10 is a schematic diagram showing a configuration of a variation of the apparatus of the present invention.
Figure 11:
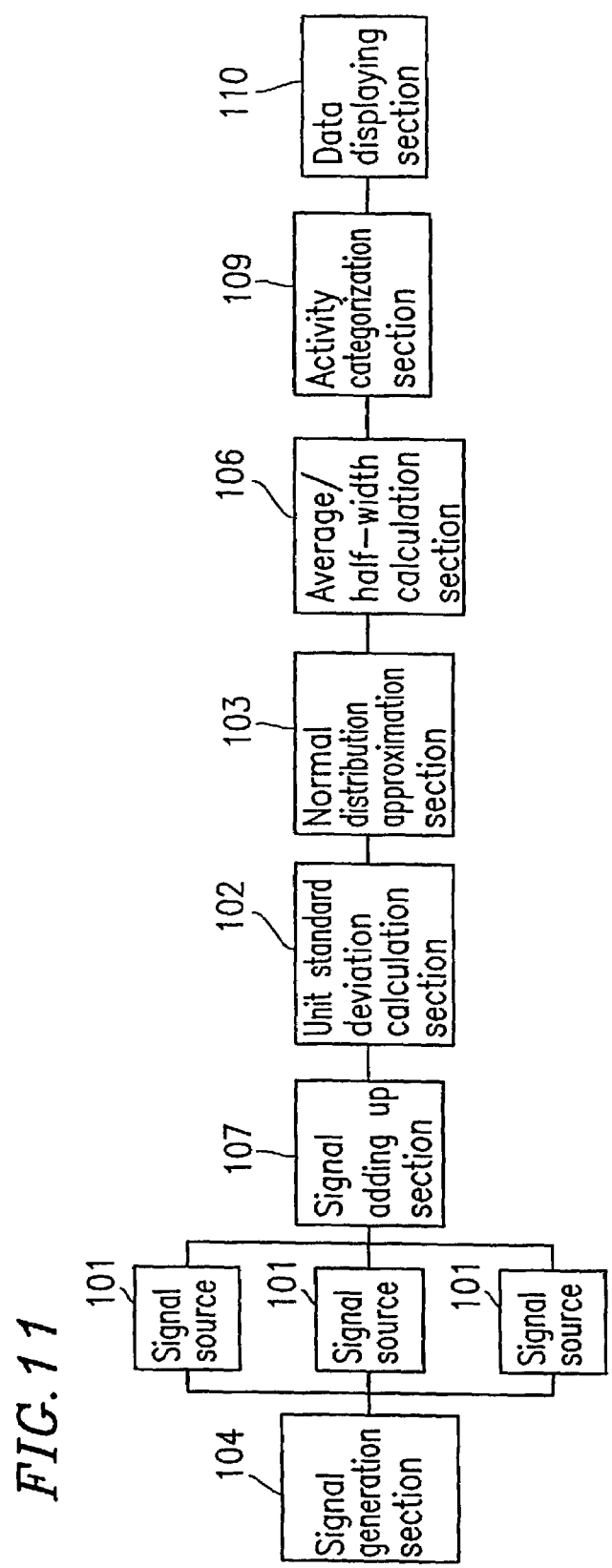
FIG. 11 is a schematic diagram showing a configuration of a variation of the apparatus of the present invention.

Note that the apparatus shown in FIG. 8 or 9 is used in the above-described examples, but alternatively, an apparatus shown in FIG. 10 or 11 may be used in place of the apparatus of FIG. 8 or 9.

The apparatus shown in FIG. 10 comprises a sample number categorization section indicated by reference numeral 111 in addition to the apparatus of FIG. 8.

The apparatus shown in FIG. 11 is the same as the apparatus of FIG. 9, except that the apparatus of FIG. 11 comprises a plurality of signal sources 101 comprising the above-described device of the present invention and further comprises a signal adding up section 107 for adding up signals from the signal sources 101 and the a signal generation section 104 for stimulating the signal sources 101.

A method and apparatus according to the present invention for measuring physicochemical changes emitted by a biological sample, such as a cell and a tissue, can extract a significant signal associated with the opening or closing of an ion channel from an extracellular measurement, which cannot be conventionally detected. Particularly, the present invention provides a method for measuring and categorizing the ion channel activity of a whole cell, where a simple device requiring substantially no specialized control apparatus can be used to easily carry out measurement in a short time and, since substantially no chemical substance is used, it is not required to consider a side effect or a change in fluorescence sensitivity over time. The present invention also provides a drug screening method and apparatus using the above-described method.

A method according to the present invention for measuring physicochemical changes emitted by a cell and a tissue can be applied to drug screening. For example, in the case of measurement of an electrophysiological cellular function, a significant signal is extracted from a captured signal as a digital signal, and measured and categorized, so that the present invention is very useful for high-speed drug screening applications.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A device for detecting a physicochemical change in a biological sample, comprising:
   at least one measuring electrode formed of a conductive material;
   a porous film;
   a conductor connected to the measuring electrode;
   a support substrate for supporting the porous film;
   a cell isolation portion provided on a surface of the porous film, for defining at least one chamber for accommodating a biological sample;
   a suction portion to be coupled in fluid communication with the biological sample in the chamber through the porous film;
   wherein the at least one measuring electrode is provided on a rear side of the porous film so as to extend into the porous film, and the biological sample is provided on a surface of the porous film, and the porous film is sandwiched between the biological sample and the at least one measuring electrode.

2. A device according to claim 1, further comprising a plurality of electrodes, and wherein each measuring electrode and the conductor connected thereto are insulated from the other measuring electrodes and the conductors thereto, so that the measuring electrodes can perform detection independently from each other.

3. A device according to claim 2, wherein each measuring electrode and the conductor connected thereto are insulated from the other measuring electrodes and the conductors thereto by an insulating resin injected to the porous film.

4. A device according to claim 2, wherein each measuring electrode and the conductor connected thereto are insulated from the other measuring electrodes and the conductors thereto by adhesive for adhering the cell isolation portion provided on the porous film to the porous film.

5. A device according to claim 1, further comprising:
   at least one reference electrode,
   wherein the measuring electrode is provided on a rear side of the porous film under the chamber, a reference electrode is provided on an inner wall of the chamber, and a conductor connected to the reference electrode is provided on an upper side of the cell isolation portion.

6. A device according to claim 5 wherein the cell isolation portion is made of an insulating material.

7. A method for measuring a physicochemical change in a biological sample of interest, comprising the steps of:
   providing a device according to claim 5;
   placing the biological sample of interest in the at least one chamber for accommodating the biological sample of interest; and
   detecting a change in the physiochemical characteristic of the biological sample of interest.

8. A method according to claim 7, wherein the characteristic are impedances of the reference electrode and the measuring electrode, and the impedance of the measuring electrode is lower than the impedance of the reference electrode.

9. A method according to claim 7, wherein the characteristic are frequency characteristics of the reference electrode and the measuring electrode, the impedance of the measuring electrode at about 10 Hz to about 10 kHz is smaller than the impedance of the reference electrode at about 10 Hz to about 10 kHz.

10. A method according to claim 8, wherein the impedance of the reference electrode is about 5 or more times as great as the impedance of the measuring electrode.

11. A method according to claim 7, wherein the characteristic selected from the group consisting of the impedance of the reference electrode: the impedance of the measuring electrode=5:1 and the volume of the electrolyte immersing the reference electrode: the volume of the electrolyte immersing the measuring electrode=5:1.

12. A method according to claim 7, wherein the step of detecting the physicochemical characteristic of the biological sample of interest comprises the steps of:
  (a) recording a physiochemical signal emitted from the biological sample of interest as a time-series signal value;
  (b) sampling the time-series signal value to obtain a plurality of groups of extracted data consisting of a plurality of values, and calculating a standard deviation of each of the plurality of groups;
  (c) calculating an average of each of the standard deviations; and
  (d) detecting a change in the physiochemical characteristic of the biological sample based on the average.

13. A method according to claim 7, wherein the step of detecting the physicochemical characteristic of the biological sample of interest comprises the steps of:
  (a) recording a physiochemical signal emitted from the biological sample of interest as a time-series signal value;
  (b) sampling the time-series signal value to obtain a plurality of groups of extracted data consisting of a plurality of values, and calculating a standard deviation of each of the plurality of groups;
  (c) dividing the standard deviations into a plurality of classes having a predetermined size of standard deviation as a unit, and obtaining a distribution indicating physicochemical characteristics of the plurality of groups of extracted data belonging to the classes;
  (d) approximating the distribution to a normal distribution;
  (e) calculating an average and a half-width of the resultant normal distribution;
  (f) optionally repeating (b) to (e); and
  (g) detecting a change in the physicochemical characteristic of the biological sample based on the average and half-width.

14. A method according to claim 13, wherein the steps (b) to (e) are repeated and the number of the time-series signal values to be sampled is changed in each repetition.

15. A method according to claim 13, wherein before the step (b), the method further comprises adding up the time-series signal values emitted by a plurality of biological samples of interest provided in the reaction systems.

16. A method according to claim 15, wherein before the step (a), the method further comprises simultaneously stimulating the plurality of the biological samples of interest.

17. A method according to claim 7, wherein the step of detecting a change in the physicochemical characteristic of the biological sample of interest, comprises:
  (a) recording a physiochemical signal emitted from the biological sample of interest as a time-series signal value;
  (b) sampling the time-series signal value to obtain a plurality of groups of extracted data consisting of a plurality of values, and calculating a standard deviation of each of the plurality of groups;
  (c) dividing the standard deviations into a plurality of classes having a predetermined size of standard deviation as a unit, and obtaining a distribution indicating physicochemical characteristics of the plurality of groups of extracted data belonging to the classes;
  (d) approximating the distribution by curvilinear approximating analysis selected from the group consisting of exponential decreasing analysis, exponential increasing analysis, Gaussian distribution, Lorentz distribution, a analysis, multiple peak analysis, and nonlinear analysis; and
  (e) detecting a change in the physicochemical characteristic of the biological sample based on gradients before and after a peak on the approximated curve obtained by the step (d).

18. A method according to claim 12, wherein the sampling in the step (b) is carried out in a time-series manner.

19. A method according to claim 12, wherein the sampling in the step (b) is carried out at random.

20. A method according to claim 12, wherein the sampling in the step (b) is carried out a plurality of times from initial data a in a time-series manner and a plurality of times from data b recorded at a predetermined time after the initial data a in a time-series manner.

21. A method according to claim 13, wherein the sampling in the step (b) is carried out a plurality of times from initial data a in a time-series manner and a plurality of times from data b recorded at a predetermined time after the initial data a in a time-series manner.

22. A method according to claim 7, wherein the step of detecting a change in the physicochemical characteristic of the biological sample of interest, comprises:
  (a) recording a physiochemical signal emitted from the biological sample of interest as a time-series signal value;
  (b) sampling the time-series signal value to obtain a plurality of groups of extracted data consisting of a plurality of values, and calculating a standard deviation of each of the plurality of groups;
  (c) sampling the resultant standard deviations to obtain a plurality of groups of extracted standard deviations consisting of a plurality of values, and calculating an average of each of the plurality of groups of extracted standard deviations; and
  (e) obtaining an index value detecting a change in the physicochemical characteristic of the biological sample based on a time of occurrence of the time-series signal value when the average reaches a predetermined threshold.

23. A method according to claim 12, wherein the biological sample of interest is a cell, and the physiochemical signal is a signal associated with activation of an ion channel or receptor of the cell, or actuation of an intracellular signal transduction system.

24. A method according to claim 13, wherein the step (a) is carried out in the presence of a standard chemical substance having a known action on the biological sample, and in the presence of a subject chemical substance, respectively, and the step (f) is carried out with concentrations of the standard chemical substance and the subject chemical substance being changed, respectively, and
  the method further comprises comparing changes in the physicochemical characteristic in the presence of the standard chemical substance obtained in the step (g) with a change in the physicochemical characteristic in the presence of the subject chemical substance obtained in the step (g), and characterizing an action of the subject chemical substance on the biological sample.

* * * * *